United States Patent [19]

Minor

[11] Patent Number: 5,387,230
[45] Date of Patent: Feb. 7, 1995

[54] SUNBATHING PROTECTION APPARATUS

[76] Inventor: Nathaniel Minor, 5835 Beaumont St., Philadelphia, Pa. 19143

[21] Appl. No.: 142,246

[22] Filed: Oct. 22, 1993

[51] Int. Cl.$^6$ ............................................. A61N 5/06
[52] U.S. Cl. .......................................... 607/95; 5/656; 5/657
[58] Field of Search ..................... 607/88, 94–95, 607/96, 114; 600/21–22; 362/217–218, 223–224, 230–231; 297/180, 184; 5/421–423, 656–657

[56]  References Cited

U.S. PATENT DOCUMENTS

| | | | |
|---|---|---|---|
| 2,653,612 | 9/1953 | Hooe | 607/95 |
| 3,625,434 | 12/1971 | Kitover | 607/95 X |
| 3,835,482 | 9/1974 | Tersch | 607/95 X |
| 4,136,412 | 1/1979 | Wilhelm | 607/95 X |
| 4,161,180 | 7/1979 | Tiger | 607/95 |
| 4,200,360 | 4/1980 | Mutzhas . | |
| 4,320,744 | 3/1982 | Fodor et al. | 607/95 X |
| 4,379,588 | 4/1983 | Speice | 607/95 X |
| 4,660,561 | 4/1987 | Nielsen . | |
| 4,793,668 | 12/1988 | Longstaff . | |
| 4,798,427 | 1/1989 | Sear . | |
| 4,888,525 | 12/1989 | Nilssen . | |
| 5,066,082 | 11/1991 | Longstaff . | |
| 5,085,212 | 2/1992 | DeCosta | 607/95 |
| 5,088,514 | 2/1992 | House et al. . | |

FOREIGN PATENT DOCUMENTS

| | | | |
|---|---|---|---|
| 3927695 | 2/1991 | Germany | 607/95 |
| 3927301 | 4/1991 | Germany | 607/95 |

Primary Examiner—Angela D. Sykes
Attorney, Agent, or Firm—Paul and Paul

[57]  ABSTRACT

A sunbathing apparatus is shown which is adapted for filtering any predetermined wavelength or wavelengths of light from passing therethrough. The sunbathing apparatus includes a frame which is adapted for providing a rigid support structure. Interchangeable panel members are also provided which are adapted for removably engaging the frame during use of the device. The interchangeable panel members are adapted for filtering the predetermined wavelength or wavelengths of light depending on the particular specifications of the panel member. A support device for supporting the user of the sunbathing apparatus is also included. The support device is adapted for being received within the sunbathing apparatus for receiving the user of the device.

27 Claims, 2 Drawing Sheets

SUNBATHING PROTECTION APPARATUS

BACKGROUND OF THE INVENTION

1. Field of the Invention

The present invention relates generally to sunbathing devices and more particularly to sunbathing devices which are adapted for affording an individual protection from the rays of the sun.

2. Background of the Invention

For years people have enjoyed the benefits of sunbathing in order for improving their physical appearance and also for promoting social interaction and general relaxation. However, it has become known that prolonged exposure to the sun can lead to numerous health related problems ranging from headaches, dry skin or sun burn to possibly skin cancer or cataracts in some circumstances. In particular, in recent years it has become known that excessive natural exposure to shortwave ultra-violet light (UV-B; 290–320 nm) is directly linked to skin cancer, including melanoma and other related disorders. This danger from UV-B light has been greatly escalated recently due to unexpected ozone decay occurring in the upper atmosphere from a build-up of manmade chemicals, such as chlorofluorocarbons and bromines. The ozone layer is a naturally occurring belt of gases approximately 10 to 30 miles high which operates to block the suns potentially harmful ultraviolet rays.

Other light extends from the UV-B region into longwave ultraviolet light (UV-A; 320–400 nm), visible or white light (400–700 nm) and finally infra-red light (ranging from 700–15,000 nm). UV-A light has been considered to be harmless at natural intensities and operates to promote skin tanning. Visible and infra-red light have also been considered safe at natural intensities, although excessive exposure has been found to lead to dehydration and heat or sun stroke in some circumstances, or possibly skin cancer from excessive visible light exposure.

Many different types of devices have been developed in order to provide protection from the harmful effects of the sun's rays. These range from devices such as umbrellas which operate to totally prevent the passage of the sun's rays to screen devices which are adapted to falter specific wavelengths of the sun's light.

One problem which has been observed is that such prior art devices do not allow the user of the device to alter the amount or particular wavelengths of light according to the needs of that particular user. For instance, some individuals who are sensitive to the sun although still desire to develop a sun tan may require that most of the sun's rays should be shielded. However, these same individuals during cloudy weather or other individuals who are not sun sensitive may desire to allow the passage of additional light rays within the visible and infra-red light regions, for example, while still shielding the harmful UV-B light. In other instances, however, the same individuals may choose to block all of the sun's rays in order to prevent any exposure to the sun.

Because of these and other shortcomings associated with sun bathing and protection devices presently employed, there now exists a need for a simple and portable device which is capable of filtering any desired wavelength or wavelengths of light depending on the needs of the user.

SUMMARY OF THE INVENTION

The present invention provides a sunbathing apparatus which is adapted for filtering any predetermined wavelength or wavelengths of light from passing therethrough. For this purpose, the sunbathing apparatus of the present invention includes a frame means which is adapted for providing a rigid support structure. Interchangeable panel means also are included which are adapted for removably engaging the frame means in order for filtering the predetermined wavelength or wavelengths of light.

The present invention also provides a support device which is adapted for use in a sunbathing apparatus. The support device of the present invention is adapted for being received within the sunbathing apparatus in order for supporting the user of the device. For this purpose, the support device can include means for supporting the user of the device which includes at least first and second members and hinge means. The hinge means is connected to the first and second members and is adapted for rotation of the first member relative to the second member for setting a position thereof. A retaining means is also included which is adapted for fixing the position of the first member relative to the second member upon rotation of the first member. The support device of the present invention can also be comprised of an inflatable member which includes at least one pocket formed therein which is adapted for removably receiving and retaining a quantity of ice.

In accordance with the present invention, an object is to provide a sunbathing apparatus which is adapted to filter any desired wavelength or wavelengths of light depending on the needs of the user.

It is another object of the present invention to provide a support device for use in a sunbathing apparatus which will promote both comfort and relaxation for the user thereof.

These and other objects of the present invention will become more readily apparent when taken into consideration with the following description and the attached drawings.

DETAILED DESCRIPTION OF THE PREFERRED EMBODIMENTS

Figure 1:
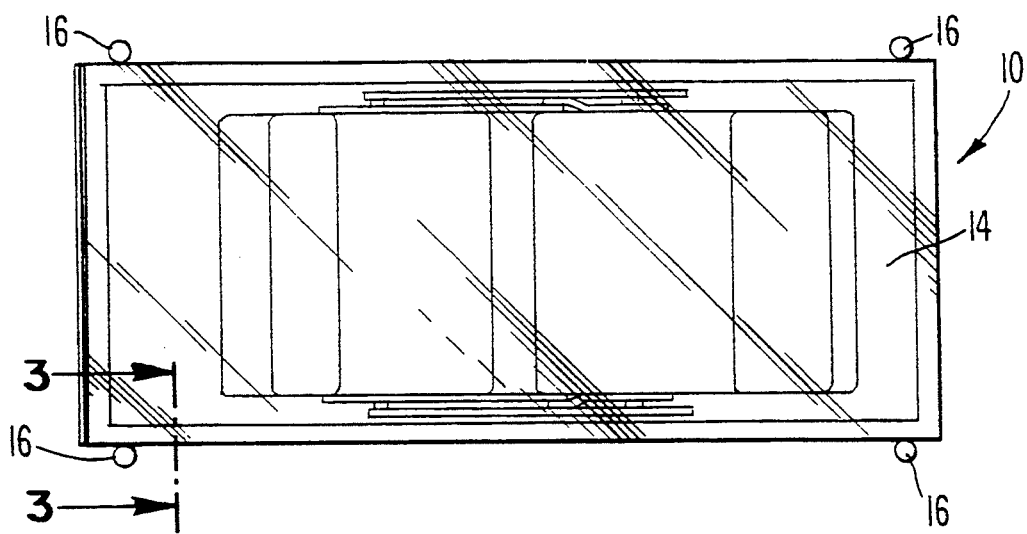
FIG. 1 is a top plan view of a sunbathing apparatus according to a first preferred embodiment of the present invention, the sunbathing apparatus including a first preferred embodiment of a user support in accordance with the present invention disposed therein.
Figure 2:
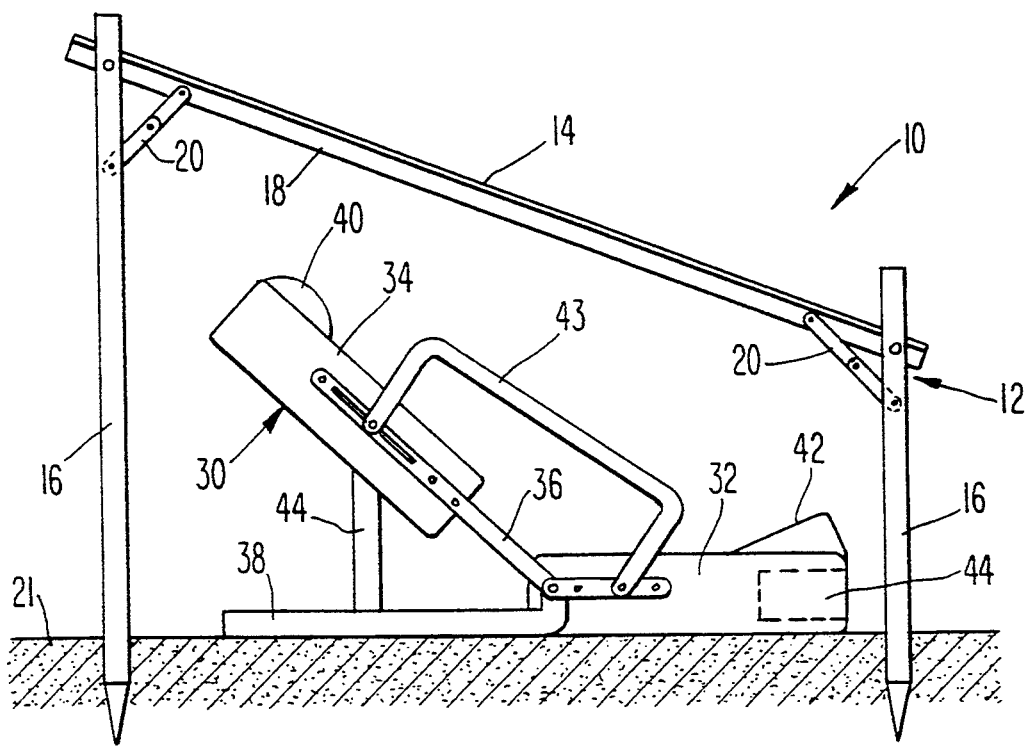
FIG. 2 is a side elevational view of the sunbathing apparatus shown in FIG. 1.
Figure 3:
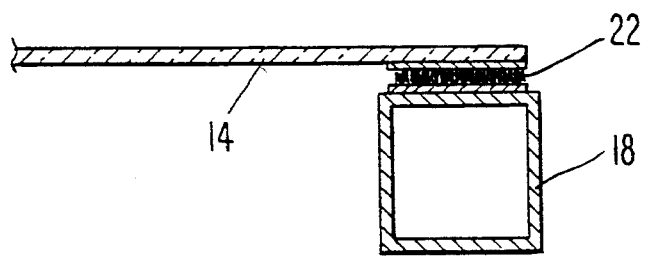
FIG. 3 is a sectional elevational view of the sunbathing apparatus of FIG. 1 taken along the line 3—3.

Referring now to the drawings in detail, wherein like reference numerals indicate like elements throughout the several views, there is shown in FIGS. 1–3 a first preferred embodiment of a sunbathing apparatus 10 according to the present invention. The sunbathing apparatus 10 as shown comprises a frame means 12, interchangeable panel means 14 and a user support means 30. In the present embodiment, the frame means 12 comprises at least two, but preferably four support means 16 as shown and a containment means 18. The containment means 18 is connected by conventional techniques such as by spot welding or by riveting or the like proximate each corner with each respective support means 16. In some instances, a reinforcement member 20 can also be included in connection with the containment means 18 proximate each end thereof and the support means 16. The reinforcement member 20 is secured to the containment means 18 and support means 16 by conventional techniques, such as by riveting or a screw nut combination or the like and is adapted for reinforcing the connection between the containment means 18 and support means 16.

As shown in this embodiment, the support means 16 is supported directly within the ground 21, however in other circumstances such may be supported within the sand or the like for the same purpose. In this regard, the support means 16 is formed including a substantially spiked end portion which is adapted to be driven or otherwise received within the ground in order for supporting the frame means 12. As to the foregoing elements of the frame means 12, such can be manufactured by conventional techniques from any suitable material, such as stainless steel or wood.

The interchangeable panel means 14 as shown comprises a series of panel members which are each adapted to filter a specific wavelength or combination of wavelengths of light. For example, one panel member of the interchangeable panel means 14 can be adapted to filter all of the UV-B light (290–320 nm) and partial of the UV-A light, such as in a range from 320–360 nm. The interchangeable panel means 14 according to the present invention can comprise conventional filtering shields manufactured of any suitable filtering materials, such as glass, thermoplastic or fiber combinations.

As shown in FIGS. 2 and 3, the interchangeable panel means 14 are adapted to be received onto the frame means 12 upon the containment means 18. In this embodiment, the interchangeable panel means 14 can also be adapted to be secured onto the frame means 12 upon receipt thereon. In this regard, preferably either the interchangeable panel means 14 or the containment means 18 are provided with at least one hook component (such as sold under the velcro ® trademark) mounted on a section thereon which is adapted to engage a corresponding pile component mounted on the respective containment means 18 or the interchangeable panel means 14. As shown in this embodiment, the respective hook and pile components are indicated by the reference number 22 and extend along the entire length of the containment means 18 and interchangeable panel means 14.

The frame means 12 of the present embodiment can also be adapted to be disassembled and/or made foldable in order to accommodate transportation of the device. In this regard, as illustrated in FIG. 2, preferably the support means 16 is pivotally connected to the containment means 18, and the reinforcement member 20 is formed as two separate members which are hinged proximate the center thereof, in order for allowing the support means 16 to be foldable inwardly against the containment means 18 following use of the device. In addition, although not shown, the containment means 18 can also be made of two separate members which are connected by a hinge to one another proximate the center thereof in order for allowing the device to be further folded into an even more compact unit. Furthermore, the support means 16 can also be formed of two separate members which are each adapted to be screw fit into one another for use of the device.

The user support means 30 as shown in FIG. 2 includes as portions thereof a first member 32 pivotally connected to a second member 34. The first and second members 32 and 34 as shown are substantially square in shape and are manufactured from conventional materials in order for supporting the user during use, however other shapes can also be provided for this purpose. As illustrated, the first and second members 32 and 34 are pivotally connected by at least one, although preferably two rod members 36 (only one of which is visible). The rod members 36 are fixedly mounted by conventional techniques to the second member 34 proximate one end thereof and pivotally connected to the first member 32 proximate the distal end thereof. A brace member 38 is also shown extending from the pivotal connection of the rod 36 and first member 32, and positioned upon the ground in order for supporting the device during use.

As illustrated in FIG. 2, portions can also be formed extending outwardly from the first and/or second members 32 and 34 in order for supporting a portion of the body of the user. In particular, as shown in the present embodiment, a substantially convex head support 40 is shown extending outwardly from the second member 34 and a substantially triangular shaped foot support 42 is shown extending outwardly from the first member 32. A substantially elongated arm support 43 can also be provided which is shown in connection with the first and second members 32 and 34, respectively. As illustrated, the first end of the arm support 43 is pivotally attached to the first member 34 and the second end is slidably engageable with the rod members 36. In this configuration, the rod members 36 form a track adapted for receiving the arm support 43. If desired, the rod members 36 can further be included with a plurality of detent apertures therein (not shown) adapted for releasably retaining the first end of the arm support 43 in predetermined positions upon rotation of the second member 34, although other suitable methods can also be provided for this same purpose. As shown in phantom, at least one storage compartment 44 can also be provided formed within the first and/or second members 32, 34 in order for receiving and retaining a plurality of objects therein, for example such as a radio, bottles, etc.

In operation, the second member 34 is pivoted in relation to the first member 32 in order for adjusting the position thereof during use. A brace member 44 can also be provided pivotally connected to the second member 34 which is adapted to engage the brace member 38 upon rotation in order for providing additional support thereof.

Figure 4:
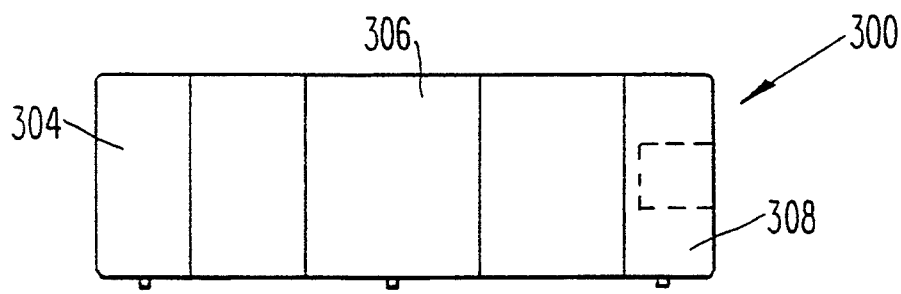
FIG. 4 is a top plan view of a user support in accordance with a second preferred embodiment of the present invention.
Figure 5:
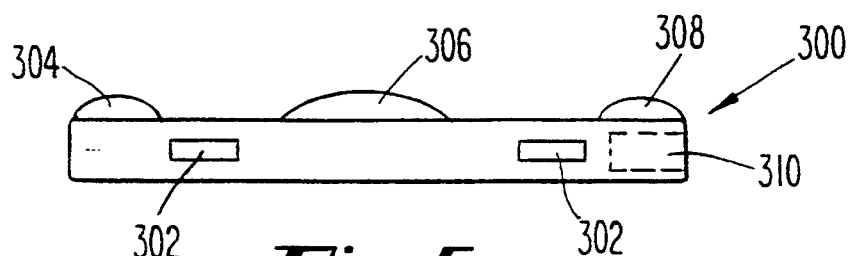
FIG. 5 is a side elevational view of the user support of FIG. 4.

In FIGS. 4 and 5 is shown a second preferred embodiment of the user support means according to the present invention. In this embodiment, the user support means 300 comprises an inflatable member manufactured of thermoplastic, rubber or the like. As best seen in FIG. 5, when inflated, the user support means 300 includes at least one air pocket formed therein, preferably the two air pockets 302 are provided which are adapted for receiving an ice pack or similar. In this embodiment, the pockets 302 are positioned so as to contact the middle of the torso and the region proximate the knee of its user during use, however other positions can also be provided for this same purpose. Furthermore, similar to that described in relation to the support means 30, the support means 300 can also be provided with portions extending upwardly therefrom adapted for supporting a portion of the user's body during use. In this regard, as shown in FIGS. 4 and 5, three inflatable supports 304, 306 and 308 are shown provided for supporting the head, back and feet of the user, respectively. Further, as shown in phantom in FIG. 5, at least one storage compartment 310 can also be provided therein for the same purpose as that in relation to the support means 30.

Figure 6:
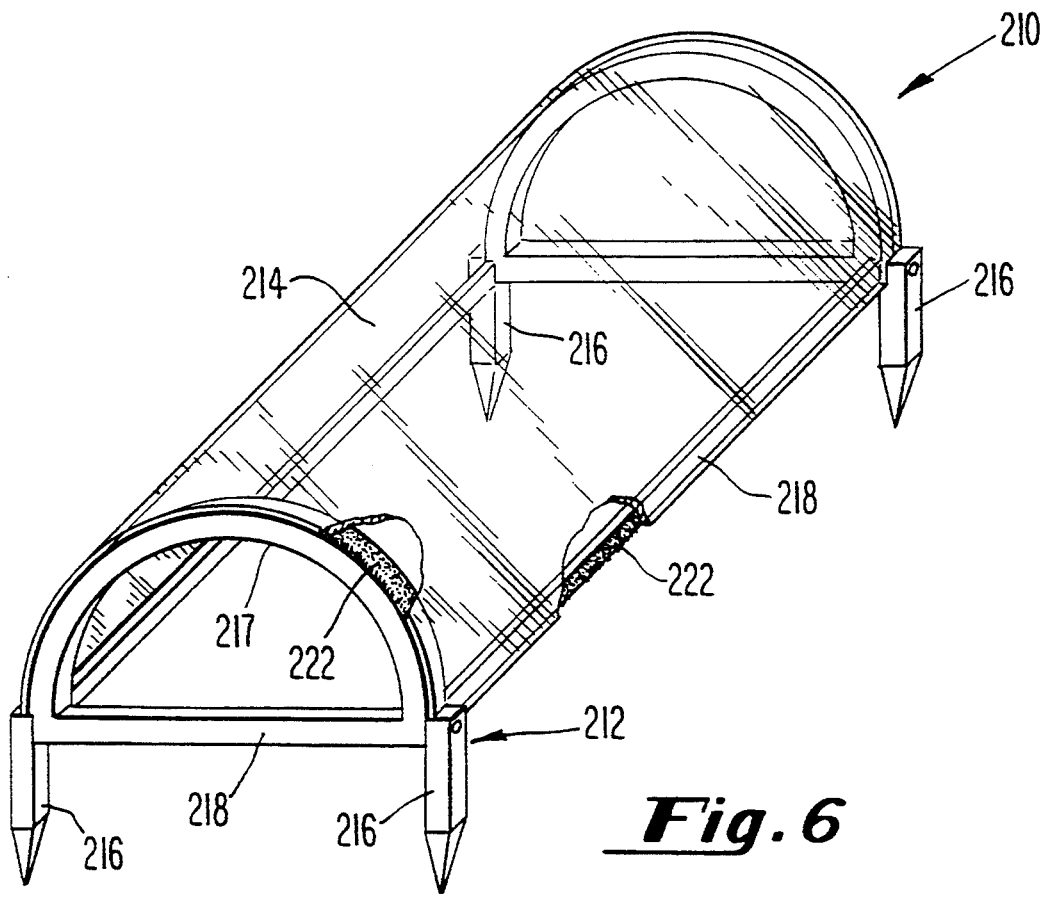
FIG. 6 is a perspective view of a sunbathing apparatus according to a second preferred embodiment of the present invention.

In FIG. 6 is shown a second preferred embodiment of the sunbathing apparatus according to the present invention. In this embodiment, portions corresponding to that designated in reference with the first embodiment are designated by the reference numbers 200. In this embodiment, the sunbathing apparatus 210 includes as portions thereof a frame means 212 and interchangeable panel means 214. Although not shown, the sunbathing apparatus 210 is adapted to receive the user support means 30 or 300 in the same manner as that indicated above. The frame means 212 as shown consistent with the frame means 12 described earlier comprises a support means 216 and a containment means 218 in connection therewith. A support member 217 comprising a substantially convex member is also provided in connection with the containment means 218 proximate the support means 216. As shown, the support member 217, containment means 218 and support means 216 are each included with apertures therethrough adapted for receiving a bolt for connection by a nut. Although in the present embodiment, a bolt and nut are utilized for connection of the foregoing members, it should be understood that any conventional means for connection may be employed for this same purpose.

As shown, the interchangeable panel means 214 comprises substantially convex members which are each adapted to be received onto the support member 217 and containment means 218 of the frame means 212. Similar to that described in relation to the first embodiment, corresponding hook and pile components 222 can also be provided mounted on the containment means 218 and support member 217, respectively, and the interchangeable panel means 214 for securing the connection therebetween. Furthermore, the support means 216 is also formed including a substantially spike end portion which is receivable within the ground, sand or the like during use of the device.

In addition, in some instances, the support member 217 can also be provided with a hook or pile member adapted for receiving a section of fabric or similar, preferably canvas, for covering the semi-circular opening formed therein (not shown). As such, in this configuration, the sunbathing apparatus 210 will comprise an enclosed environment within the frame means 212 and interchangeable panel means 214.

It will be recognized by those skilled in the art that changes may be made by the above-described embodiments of the invention without departing from the broad inventive concepts thereof. For example, although the user support means 30 and 300 are disclosed, it should be understood that any suitable user support means can also be used for this same purpose. In addition, the support means 16 and 216, which are shown having substantially spiked end portions which are receivable within the ground for support of the device, can be formed having any suitable configuration in order for accommodating use of the device upon any suitable surface. For instance, the support means 16 and 216 can be formed having substantially flat end portions in order for accommodating use of the device upon a solid material, such as concrete or asphalt. Furthermore, in other instances, the substantially spiked end portions of the support means 16 and 216 can be received within a support base placed upon the ground in order for accommodating use thereof without placing the spiked portions within the ground itself. For example, the support base, which can be manufactured from any suitable rigid material, such as rubber or stainless steel, is configured to receive and retain the substantially spiked end portion of the support means 16, 216. For example, the support base can be provided with an aperture therein which is formed corresponding in configuration to the support means 16, 216. In some circumstances, the aperture can be formed slightly smaller than the support means 16, 216, or otherwise adapted to exert a suitable amount of pressure thereon when received, in order to ensure engagement within the support base. The side opposite the aperture is formed to maintain contact with the ground or other surface for supporting the structure during use. It is understood, therefore, that this invention is not limited to the particular embodiments disclosed, but it is intended to cover all modifications which are within the scope and spirit of the invention as defined by the appended claims.

I claim:

1. A sunbathing kit adapted for filtering any predetermined wavelength or wavelengths of light from passing therethrough; the sunbathing kit comprising:

frame means adapted for providing a rigid support structure; and interchangeable panel means removably engaging the frame means adapted for filtering the predetermined wavelength or wavelengths of light, wherein the interchangeable panel means comprises a plurality of separate panel members, with each panel member filtering a particular wavelength or wavelengths of light, whereby each panel member is adapted for being placed into engagement one at a time with the frame means by a user, with the frame means supporting the panel members on assembly, wherein the user chooses the particular panel member to be used depending on the wavelength or wavelengths of light which are desired to be filtered from passing therethrough and into contact with the user wherein each panel member is further capable of being removed by the user from the frame means following use of the device for disassembly.

2. A sunbathing kit according to claim 1, wherein each of the panel members comprises a unitary member of a substantially rigid material.

3. A sunbathing kit according to claim 2, wherein the frame means further includes at least two support means adapted for maintaining the position of the frame means and containment means, with the containment means being in connection with the two support means and adapted for receiving the panel members on assembly, wherein the containment means comprises at least two opposing generally elongated portions, with each portion having an upper Side and a lower side, and wherein each of the panel members have an upper surface and a lower surface, whereby the upper sides of the two opposing generally elongated portions are in engagement with the lower surface of the panel members for support thereof on assembly.

4. A sunbathing kit according to claim 3, wherein the panel members each include associated therewith and along at least one portion thereof a first means, and wherein the frame means includes associated therewith and along at least one portion thereof a second means, wherein the first means and the second means are releasably engageable to each other for removably engaging the panel members to the frame means.

5. A sunbathing kit according to claim 4, wherein the first means comprises at least one hook component and the second means comprises at least one pile component.

6. A sunbathing kit according to claim 4, wherein the first means comprises at least one pile component and the second means comprises at least one hook component.

7. A sunbathing kit according to claim 4, further comprising means for supporting the user of the device adapted for being receivable within the frame means and between the panel members and the ground, sand or the like for receiving and supporting the user of the device.

8. A sunbathing kit according to claim 7, wherein the means for supporting the user of the device comprises at least first and second members and hinge means, with the hinge means connected to the first and second members adapted for rotation of the first member relative to the second member for setting a desired position thereof for comfort of the user.

9. A sunbathing kit according to claim 8, further including arm support means pivotally connected to the first member and slidably engaging the second member adapted for supporting the arms of the user, and wherein the means for supporting the user of the device, further includes at least One portion projecting outwardly therefrom adapted for receiving and supporting a portion of the body of the user for comfort.

10. A sunbathing kit according to claim 9, wherein the second member includes a substantially planar upper surface having a foot support projecting outwardly therefrom, with the foot support including a front end and a back end and is tapered outwardly away from the second member in a direction from the first end toward the second end, and wherein the first member includes a substantially planar upper surface having a head support projecting outwardly therefrom, with the head support comprising a substantially convex member.

11. A sunbathing kit according to claim 7, wherein the means for supporting the user of the device comprises an inflatable member generally elongated in a first direction for receiving and supporting the user when sunbathing, wherein the inflatable member includes chamber means for receiving a quantity of air for inflation of the inflatable member for use, the inflatable member further including at least one pocket means for removably receiving and retaining a quantity of ice for cooling of the user, wherein the at least one pocket means is isolated from both the air chamber means and user during sunbathing.

12. A sunbathing kit according to claim 11, wherein the inflatable member further includes at least one inflatable portion extending outwardly therefrom for supporting a portion of the body of the user, wherein the inflatable portion is generally elongated in a second direction substantially perpendicular the generally elongated first direction of the inflatable member.

13. A support device in a sunbathing kit adapted for filtering any desired predetermined wavelength or wavelengths of fight from passing therethrough, the support device adapted for being receivable within the sunbathing and comprising:

means for supporting the user of the device including at least first and second members and hinge means, with the hinge means connected to the first and second members and adapted for rotation of the first member relative to the second member for setting a desired position thereof for comfort of the user; and retaining means adapted for fixing the position of the first member relative to the second member upon rotation of the first member;

the sunbathing kit comprising:

frame means adapted for providing a rigid support structure; and interchangeable panel means removably engaging the frame means adapted for faltering the predetermined wavelength or wavelengths of fight, wherein the interchangeable panel means comprises a plurality of separate panel members, with each panel member filtering a particular wavelength or wavelengths of light, whereby each panel member is adapted for being placed into engagement one at a time with the frame means by a user, with the frame means supporting the panel members on assembly, wherein the user chooses the particular panel member to be used depending on the wavelength or wavelengths of fight which are desired to be filtered from passing therethrough and into contact with the user, wherein each panel member is further capable of being removed by the user from the frame means following use of the device for disassembly.

14. A support device according to claim 13, further including arm support means pivotally connected to the first member and slidably engaging the second member adapted for supporting the arms of the user.

15. A support device according to claim 13, wherein the support device further comprises at least one portion extending outwardly therefrom adapted for receiving and supporting a portion of the body of the user for comfort.

16. A support device according to claim 15, wherein the first member includes a substantially planar upper surface having a head support projecting outwardly therefrom and the second member includes a substantially planar upper surface having a foot support projecting outwardly therefrom.

17. A support device according to claim 16, wherein the foot support includes a front end and a back end and is tapered outwardly away from the second member in a direction from the first end toward the second end, and wherein the head support comprises a substantially convex member.

18. A support device according to claim 13, wherein the user support means further includes at least one storage compartment provided therein.

19. A support device for use in a sunbathing apparatus adapted for filtering any desired predetermined wavelength or wavelengths of light from passing therethrough, the support device adapted for being receivable within the sunbathing apparatus and comprising:

an inflatable member generally elongated in a first direction for receiving and supporting a user when sunbathing, wherein the inflatable member includes chamber means for receiving a quantity of air for inflation of the inflatable member for use, the inflatable member further including at least one pocket means for removably receiving and retaining a quantity of ice for cooling of the user, wherein the at least one pocket means is isolated from both the air chamber means and user during sunbathing.

20. A support device according to claim 19, wherein the inflatable member further includes at least one inflatable portion extending outwardly therefrom for supporting a portion of the body of the user, wherein the inflatable portion is generally elongated in a second direction substantially perpendicular the generally elongated first direction of the inflatable member.

21. A support device according to claim 19, wherein the inflatable member includes three inflatable portions extending outwardly therefrom adapted for supporting the head, back and feet of the user, respectively, wherein the three inflatable portions are generally elongated in a second direction substantially perpendicular the generally elongated first direction of the inflatable member.

22. A support device according to claim 21, wherein the three inflatable portions are substantially convex members.

23. A support device according to claim 19, wherein the inflatable member further includes at least one storage compartment provided therein isolated from the air chamber means and at least one pocket means.

24. A sunbathing kit adapted for filtering any predetermined wavelength or wavelengths of light from passing therethrough; the sunbathing kit comprising:

frame means adapted for providing a rigid support structure;

interchangeable panel means removably engaging the frame means adapted for filtering the predetermined wavelength or wavelengths of light, wherein the interchangeable panel means comprises a plurality of separate panel members, with each adapted for filtering a particular wavelength or wavelengths of light, wherein each panel member comprises a unitary member of a substantially rigid material, whereby each panel member is adapted for being placed into engagement one at a time with the frame means by a user; with the frame means supporting the panel members on assembly, wherein the user chooses the particular panel member to be used depending on the wavelength or wavelengths of light which are desired to be filtered from passing therethrough and into contact with the user, wherein each panel member is further capable of being removed by the user from the frame means following use of the device for disassembly, the panel members each further including associated therewith and along at least one portion thereof a first means, and wherein the frame means includes associated therewith and along at least one portion thereof a second means, wherein the first means and the second means are releasably engageable to each other for removably engaging the panel members to the frame means, wherein the first means and the second means comprise at least one hook component and at least one pile component adapted for releasably engaging each other; and wherein the frame means includes at least two support means adapted for maintaining the position of the frame means and a containment means, with the containment means being in connection with the two support means and adapted for receiving the panel members on assembly, wherein the containment means comprises at least two opposing generally elongated portions, with each portion having an upper side and a lower side, and wherein each of the panel members have an upper surface and a lower surface, whereby the upper sides of the two opposing generally elongated portions are in engagement with the lower surface of the panel members for support thereof on assembly.

25. A sunbathing kit according to claim 24, further comprising means for supporting the user of the device adapted for being receivable within the frame means and between the panel members and the ground, sand or the like for receiving and supporting the user of the device.

26. A sunbathing kit according to claim 24, wherein each panel member defines a substantially planer member over the entire length thereof.

27. A sunbathing kit according to claim 24, wherein each panel member defines a substantially convex member over the entire length thereof.

* * * * *

UNITED STATES PATENT AND TRADEMARK OFFICE
CERTIFICATE OF CORRECTION

PATENT NO. : 5,387,230
DATED : February 7, 1995
INVENTOR(S) : Nathaniel Minor

It is certified that error appears in the above-indentified patent and that said Letters Patent is hereby corrected as shown below:

Column 1, line 18 after "sun" the word "bum" should be -- burn --;

Column 1, line 47 after adapted to "falter" should be -- filter --;

Column 3, line 9 after proximate each "comer" should be -- corner --;

Column 8, line 5, Claim 13 after wavelengths of "fight" should be -- light --;

Column 8, line 22, Claim 13 after adapted for "faltering" should be -- filtering --;

Column 8, line 23, Claim 13 after wavelengths of "fight" should be -- light --;

UNITED STATES PATENT AND TRADEMARK OFFICE
CERTIFICATE OF CORRECTION

PATENT NO.   : 5,387,230
DATED        : February 7, 1995
INVENTOR(S)  : Nathaniel Minor It is certified that error appears in the above-indentified patent and that said Letters Patent is hereby corrected as shown below:

Column 8, line 34, Claim 13 after wavelengths of "fight" should be -- light --.

Signed and Sealed this

Fourth Day of July, 1995

Attest:

BRUCE LEHMAN

*Attesting Officer*    *Commissioner of Patents and Trademarks*